United States Patent [19]

Maurer et al.

[11] Patent Number: 4,544,353
[45] Date of Patent: Oct. 1, 1985

[54] ORTHODONTIC APPLIANCE FOR DIRECT BONDING TO A TOOTH

[75] Inventors: Robert S. Maurer, Huntington Beach; Min H. Tsai, Van Nuys, both of Calif.

[73] Assignee: Unitek Corporation, Monrovia, Calif.

[21] Appl. No.: 434,016

[22] Filed: Oct. 12, 1982

[51] Int. Cl.⁴ .................................................. A61C 7/00
[52] U.S. Cl. ......................................................... 433/9
[58] Field of Search ............................................ 433/9

[56] References Cited

U.S. PATENT DOCUMENTS

| 4,094,068 | 6/1978 | Schinhammer | 433/9 |
| 4,322,206 | 3/1982 | Webb et al. | 433/9 |
| 4,369,033 | 1/1983 | Reynolds | 433/9 |

Primary Examiner—Robert Peshock
Attorney, Agent, or Firm—Stuart E. Krieger; John J. Balser; Isaac Jarkovsky

[57] ABSTRACT

An orthodontic direct bond appliance has a body with a base. The base includes a rim extending from its periphery at an angle between about 90° and 170° so as to define a recess for receipt of bonding material. The rim shears off any excess flash.

5 Claims, 4 Drawing Figures

ORTHODONTIC APPLIANCE FOR DIRECT BONDING TO A TOOTH

BACKGROUND OF THE INVENTION

A. Field of the Invention

This invention relates generally to orthodontic appliances, and more particularly relates to the base portion of orthodontic appliances involved in direct bonding to a tooth.

B. Description of the Prior Art

The conventional method of orthodontic treatment has been through the use of metal brackets welded onto metal bands. The metal bands are mounted on the teeth requiring correction and an arch wire is attached to the brackets so that corrective forces may be applied to the teeth to properly position them within the dental arch. Problems associated with these bands include decalcification, patient discomfort and gingival irritation.

Bonding bandless brackets directly to the tooth surface was made possible as a result of the experiments by Buonocore in which tooth enamel was etched with phosphoric acid to enhance the bonding of adhesives to the tooth, (Journal of Dental Research, 34 (6) pp. 849–853, 1955).

A bandless bracket typically consists of two parts. One is the bracket body with grooves for accommodating wires which transmit corrective forces to the tooth. The other is the bracket base for supporting the bracket body and for bonding to the adhesive. Bandless brackets are made of metallic or plastic materials. While plastic brackets may be aesthetically pleasing they are too soft and deform during treatment. Plastic brackets may also discolor rapidly in the oral environment. Stainless steel brackets provide strength to withstand the forces required for the orthodontic treatment, but stainless steel brackets alone cannot be bonded effectively to the adhesive. In order to enhance the adhesion, Retief et al. (American Journal of Orthodontics 58 (1) p. 35, 1970) used brackets with slots in the bases to provide mechanical retention. U.S. Pat. No. 3,975,824 also described stainless steel brackets with undercuts to form a physical lock between the bracket base and adhesive. It is, however, labor intensive to produce these types of brackets.

It is also well-known in the art to use bonding pads which produce a mechanical interlock with the adhesive. Bonding pads are joined to the brackets by brazing, welding or sintering techniques. Brackets often are angulated on the bonding pads. Direct bond appliances with a two-part assembly are now widely used in the art.

Direct bond orthodontic appliances are attached to teeth by a widely used technique. This technique consists of three phases: applying the adhesive to the bondable surface of the appliance; putting the adhesive coated appliance onto the tooth; and cleanup of the residual adhesive.

Current orthodontic direct bond appliances are prone to fail in all three phases of the direct bond technique. Application of the adhesive to the current designs of bondable surfaces is sometimes difficult. Without a coherent layer of adhesive on the bondable surface, the appliance will fall off during treatment. Current appliances tend to skid or drift during placement on the tooth surface. Skidding destroys the initially polymerized adhesive and makes proper placement of the appliances difficult. Cleaning of residual adhesive expelled as flash from current design bases must be done with care. Improper removal of flash from the periphery of the base creates voids under the edge of the base. These voids create weak areas and lead to decalcification of the underlying tooth.

It is an object of the present invention to provide a new structure for the base portion of an orthodontic appliance for facilitating bonding of the base portion to a tooth, without the above described disadvantages.

SUMMARY OF THE INVENTION

This object is accomplished by providing for a rim projecting from the periphery of the bonding base of an orthodontic appliance. When the rim projects outward from the periphery of the bonding base forming an inside angle ranging from about 90° to about 170° with respect to said base, the bond strength achieved is substantially higher than orthodontic appliances lacking this feature. This feature of the bonding base alleviates the necessity for the practitioner to maintain critical control of his bonding technique, as he must do now with appliances presently available on the market having conventional base designs.

BRIEF DESCRIPTION OF THE DRAWINGS

The present invention may be more readily understood by referring to the accompanying drawings in which.

DESCRIPTION OF THE PREFERRED EMBODIMENT

Figure 1:
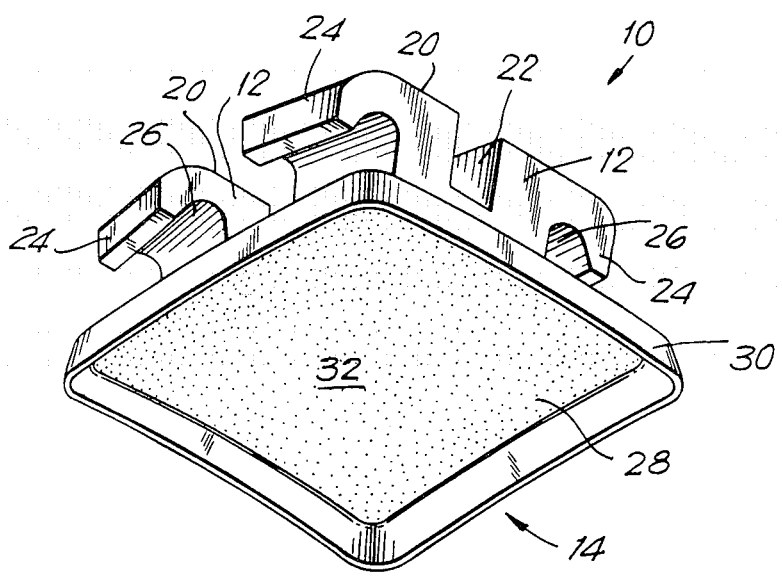
FIG. 1 shows a perspective view of an orthodontic bracket in accordance with the present invention.
Figure 2:
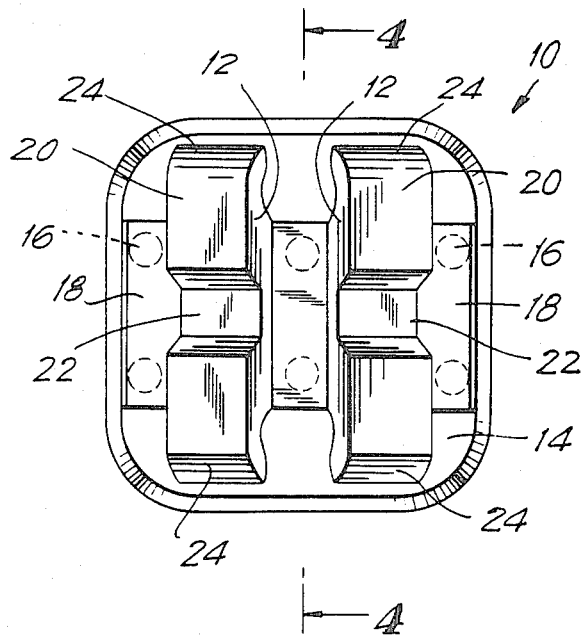
FIG. 2 shows a two-part orthodontic bracket constructed in accordance with the present invention.
Figure 3:
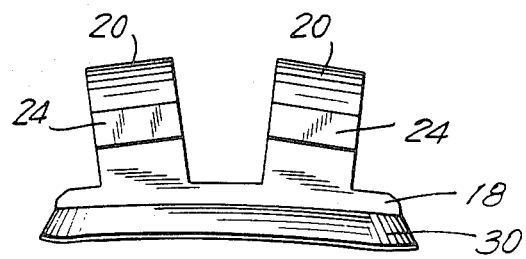
FIG. 3 shows a side elevational view of the orthodontic bracket of FIG. 2.
Figure 4:
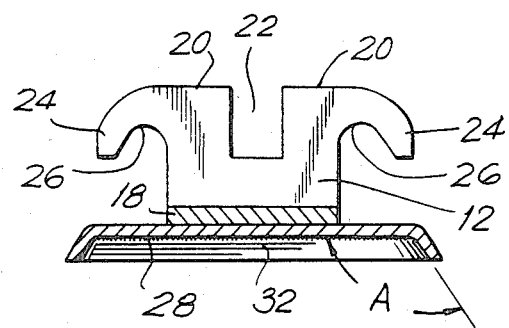
FIG. 4 shows a cross-sectional view taken along lines 4—4 of FIG. 2.

Referring now to FIGS. 1–4, a direct bond orthodontic appliance in accordance with the present invention is in the form of a stainless steel orthodontic bracket 10 shown to comprise a body and a base portion 14. The body includes two body portions 12 which may be formed integrally with the base portion, as shown in FIG. 1, or the body portions 12 may be secured to the base portion 14, for example by spot welding of supporting plate 18 to the base portion 14 as shown in phantom in FIG. 2 at 16.

The body portions 12 each have a buccal surface 20 with a slot 22. The slots 22 are aligned to receive a conventional arch wire (not shown). Each body portion 12 has a pair of overhanging wings 24 which are integrally formed on its opposite lateral edges and which extend rearwardly to define a pair of generally V-shaped notches 26.

The base portion 14 has a bonding surface 28, also referred to as the rear or lingual surface. Projecting outwardly from the periphery of the bonding surface 28 is a lip or rim 30 forming an inside angle A with the periphery of the bonding surface 28 within the range of from about 90° to about 170°. The rim 30 and bonding surface 28 define a recess 32 adapted to receive the adhesive material which bonds the bonding surface, and consequently the orthodontic bracket 10, to the surface of the tooth (not shown).

The rim 30 reduces the problems encountered with the bases currently in use. Specifically, the rim shears off any excess flash on contact with the tooth surface. The shearing of flash from the adhesive within the recess 32 permits removal of the flash without the danger of simultaneously removing adhesive from the recess 32. In addition, the orientation of the rim 30 relative to the tooth surface minimizes leakage of adhesive from under the appliance onto the tooth. Thus, danger of decalcification is minimized when a rim 30 is incorporated into the base portion 14.

The present invention facilitates an even application of a thick pad of adhesive to the bonding surface 28 of the orthodontic appliance that takes the shape of the enclosure bonded by the bonding surface 28, rim 30 and tooth surface. This pad is relatively thick compared to some direct bond coatings and reduces unwanted movement, including skidding, on the tooth surface.

Significantly, orthodontic appliances having base portions 14 equipped with a rim 30 have demonstrated a 41% increase in bond strength when compared with orthodontic appliances lacking this feature. An appliance with a rim 30, when directly bonded, withstood a tensile force up to 7.9 pounds, before the bond ruptured while direct bonding of the same appliance without a rim yielded at 5.6 pounds.

While the invention has been described above with respect to specific embodiments, it should be clear that these embodiments are given by way of example and shall not be deemed as limiting the scope of the invention, except in accordance with the claims hereof.

The invention claimed is:

1. An orthodontic direct bond appliance comprising: a body having an integral thin base portion extending therefrom, said base portion including a bonding surface wih a rim projecting from the periphery of said surface forming an inside angle with said surface ranging between about 90° to about 170°, said integral thin rim and bonding surface defining a recess adapted for receipt of bonding material, whereby the rim shears off any excess flash.

2. An orthodontic appliance as claimed in claim 1, wherein said bonding surface is substantially planar.

3. An orthodontic applicance as claimed in claim 1, wherein said body and base portion are integral.

4. An orthodontic applicance as claimed in claim 1, wherein said body is secured to said base portion.

5. An orthodontic appliance as claimed in claim 1, wherein said body and base portion form a bracket.

* * * * *